United States Patent [19]
Frezza

[11] Patent Number: 6,095,757
[45] Date of Patent: Aug. 1, 2000

[54] LIQUID DRUG INFUSION PUMP

[75] Inventor: Pierre Frezza, Charly, France

[73] Assignee: Compagnie Developpement Aguettant, Lyons, France

[21] Appl. No.: 08/983,240

[22] PCT Filed: Jul. 10, 1995

[86] PCT No.: PCT/FR95/00922

§ 371 Date: Mar. 9, 1998

§ 102(e) Date: Mar. 9, 1998

[87] PCT Pub. No.: WO97/02852

PCT Pub. Date: Jan. 30, 1997

[51] Int. Cl.[7] .................................................. F04B 49/06
[52] U.S. Cl. ........................ 417/44.1; 417/42; 417/63; 92/98 R; 92/99; 92/101; 92/103 R
[58] Field of Search ................. 417/44.1, 42, 63; 92/98 R, 99, 101, 103 R; 604/152

[56] References Cited

U.S. PATENT DOCUMENTS

| 3,976,402 | 8/1976 | Lundquist | 417/566 |
| 3,993,061 | 11/1976 | O'Leary. | |
| 4,519,792 | 5/1985 | Dawe. | |
| 4,798,589 | 1/1989 | Tseo | 604/152 |
| 4,919,596 | 4/1990 | Slate et al. | 417/18 |

FOREIGN PATENT DOCUMENTS

| 0 454 331 A1 | 10/1991 | European Pat. Off. . |
| 2 689 014 A1 | 10/1993 | France . |
| 2 715 310 A1 | 7/1995 | France . |

*Primary Examiner*—Charles G. Freay
*Attorney, Agent, or Firm*—Oliff & Berridge, PLC

[57] ABSTRACT

10 Claims, 3 Drawing Sheets

LIQUID DRUG INFUSION PUMP

BACKGROUND OF THE INVENTION

The subject of the present invention is a pump or infusing medical liquids.

These days, intravenous infusion is an essential treatment technique for severe illnesses, such as cancer for example.

The effectiveness of the treatments is directly connected to the prescribed doses and limited by the level of toxicity of the active principles. The precision of the injection is therefore an important criterion when choosing what equipment to use. Furthermore, it has been observed that, in order to respect the patient's biological patterns, an active principle should, as a preference, be injected at certain times of the day, it being possible for the rate of injection to vary throughout the period of injection in order to take into account the immediate effects that the active principle has on the organism.

Moreover, it has been observed that it was possible, and even advantageous, to combine a number of products, some of which can be injected simultaneously using the same catheter, and others injected by different routes.

One trend in modern-day medicine is the move towards treatment in the patient's own home, this being more particularly true as regards difficult pathologies such as treatment for cancer and for AIDS, which require a great deal of technology in a hospital environment and follow-up treatment at the patient's home.

Most infusion equipment currently available on the market does not take account of this trend towards care in the patient's own home. Existing portable pumps are generally heavy, cumbersome and have limited autonomy. The pumps most commonly used are peristaltic pumps, which crush a polymer or silicone tube in order to convey the product from a reservoir to the catheter feeding into the patient.

This type of apparatus has the drawback of combining technical solutions which are bulky and heavy:

To crush the tube requires a great deal of force which is obtained by a cumbersome and heavy system of rollers. The motor has to be rated to be capable of obtaining these crushing forces, and this leads to a high weight. As the power consumption of the motor is high, the motor has to be powered by a series of voluminous and heavy cells or batteries, and this is in conflict with the very idea of the pump being portable.

Another solution consists in using devices of the syringe-pusher type, in which the plunger of a syringe containing the product to be injected is driven by a stepping motor. Aside from the weight and bulk drawbacks described earlier, a system of this kind cannot generally be programmed, and is suitable only for infusing a limited volume of liquid.

Document FR-A-2,689,014 in the name of the Applicant Company describes a pump for infusing medical liquids, which has a number of ducts, that is to say can allow simultaneous infusion of a number of medical liquids, with the possibility of mixing or of not mixing these liquids within the pump, which has a very small bulk and a low weight while at the same time allowing a great deal of accuracy on the flow rate over a very broad range of flow rates which can vary, for example, from between 1 milliliter per day to 300 milliliters per hour, and which offers the patient a great deal of safety.

The pump described in this document, of the type comprising at least one cylinder and piston device for drawing up a liquid from a container and delivering this liquid into a tube connected to the patient, is characterized in that it comprises:

- a first piece in which there is made at least one metering cylinder which, containing a piston which is moved back and forth, opens into one of the faces of the piece, perpendicular to this face,
- a second piece which, resting against the face of the first piece into which each cylinder opens, comprises, opposite each cylinder, a cavity with a diameter that is greater than that of the corresponding cylinder and communicating with a liquid-supply container,
- and a leaktight and elastically deformable membrane closing off the opposite end of the cylinder to the piston, and the other face of which is on the side towards which the liquid is conveyed from a container, this membrane comprising at least one opening for the passage of the liquid and allowing the cylinder to be supplied with liquid as the piston moves in a direction that increases the volume of the cylinder, whereas it isolates the cylinder from the supply when the piston moves in the other direction, the liquid then being discharged from the cylinder through at least one port made therein close to the membrane.

In the known device, the metering chamber is delimited by a deformable membrane trapped between two parts of the piston, one part situated inside the metering chamber, and the other part situated outside the metering chamber. The two parts of the piston are joined together, for example by screwing, using a screw that passes through an orifice made in the membrane. This solution has the drawback that a perfect seal is not achieved between the liquid circuit and the outside. Furthermore, the piston needs to be coupled to the drive device so that it can be pulled and pushed. Since it is desirable for the motor to be removed by detaching the drive and programming part from the metering part, which is a wearing part, complex means need to be employed, for example a magnetic coupling using a ferromagnetic pellet formed in the piston. However, in addition to its complexity, this solution has the drawback that the attachment between the piston and the motor is relatively unpredictable.

SUMMARY OF THE INVENTION

The object of the invention is to provide a pump of the last-mentioned type, in which the seal between the liquid and the outside is strictly achieved, and in which the coupling between the drive part and the piston is achieved simply and entirely reliably.

To achieve this, in the pump to which it relates, which is of the aforementioned type, the piston is covered on its end face and on its lateral wall by an elastic membrane mounted in tension over the piston, and fixed by its peripheral edge to a stationary support independent of the piston, the means of driving the piston consisting of a device which exerts only a pushing force on the piston in the direction to make the piston enter the cylinder, and the thickness of the membrane is greater at the end face of the piston than it is at the side wall thereof, and the thicker region of the membrane has, on its outwardly-pointing face, a recess of a concave shape that more or less complements the convex shape of the membrane delimiting the cylinder.

The elastic membrane covering the piston ensures that the liquid is perfectly sealed to the outside, perfectly isolating the metering chamber. The elastic return force of the membrane is exerted on the piston and thus returns it when there is no longer any action exerted on it. All that is then required is for drive means which exert a pushing force on the piston in the direction to make it enter the cylinder, the piston tending, under the effect of the membrane relaxing, to move back as soon as it is no longer being pushed into the cylinder. It is therefore unnecessary to provide positive drive means between the driving means and the piston, simple contact being sufficient.

This shape of membrane makes it possible to avoid forming a dead space between it and the upper membrane, when the piston is in the forward position, and this makes the pump easier to prime.

According to one feature of the invention, the elastic membrane covering the piston is made of elastomer or of latex.

Advantageously, the membrane has, close to its part that covers the front face of the piston, a peripheral ring which seals it against the cylinder. This arrangement makes it possible to keep the volume of residual liquid between the chamber and the membrane constant irrespective of the working pressure.

According to one embodiment of this pump, the device for driving each piston comprises a disc with an axis orthogonal to the axis of the cylinder, the edge of which bears on the free end of the piston, and which is rotated about an axis parallel to and offset from its own axis.

Advantageously in this case, the disc, the edge of which bears against the free end of the piston, is fixed to a disc one face of which has teeth interacting with a pinion fixed to the output shaft of a geared motor unit, the two discs being fixed together with their respective axes offset.

It will be understood that the disc bearing against the free end of the piston has a centre the position of which will vary with respect to the centre of the motorized disc, by rotation about the centre of the motorized disc. This means that the driven disc will be able in succession to exert a pushing force on the piston then to release this pushing force to allow the piston to spring back under the effect of the membrane relaxing.

Advantageously, mounted on the axis of the motorized disc is a free-wheel mechanism that prevents the disc from moving in the opposite direction to the direction in which it is driven by the motor under the effect of the pulling force of the membrane when the system is stopped or not powered.

According to another feature of the invention, the motorized disc has peripheral slots intended to be detected by an optical encoder in order to determine the volume of liquid transferred, this encoder being connected to a pulse counter itself connected to a comparator which compares the measured pulses with a reference value in order to control the electrical supply to the motor.

Advantageously, the peripheral slots in the motorized disc are arranged as a sinusoidal function in order to take account of the offset between the axes of the two discs. This relative arrangement of the peripheral slots allows a constant volume to be made to correspond to the separation between two slots, even though the slots are not all equidistant.

To encourage the unit as a whole to run smoothly, the edge of the disc bearing against the piston is covered by a ball race.

In cases where the pump comprises a unit containing the programming means and the motor associated with each piston and a removable cassette allowing the various liquids to be drawn up and delivered, each piston and the membrane covering it are mounted in the cassette.

The control unit and the cassette may then be assembled simply and quickly, for example by snapping together.

BRIEF DESCRIPTION OF THE DRAWINGS

In any case, the invention will be clearly understood with the aid of the description which follows, with reference to the appended diagrammatic drawing which, by way of non-limiting example, depicts one embodiment of this pump.

DETAILED DESCRIPTION OF THE PREFERRED EMBODIMENT

Figure 1:
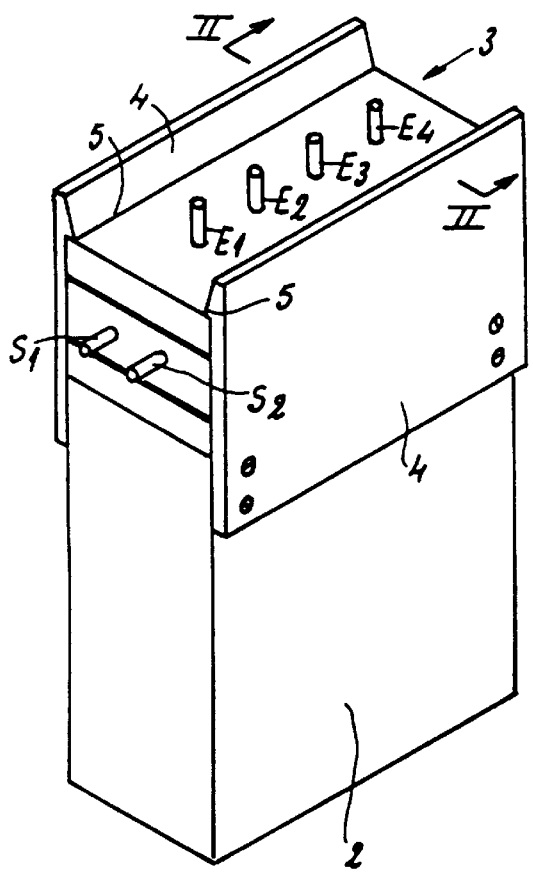
FIG. 1 is a perspective view of a pump intended to convey four separate liquids.
Figure 2:
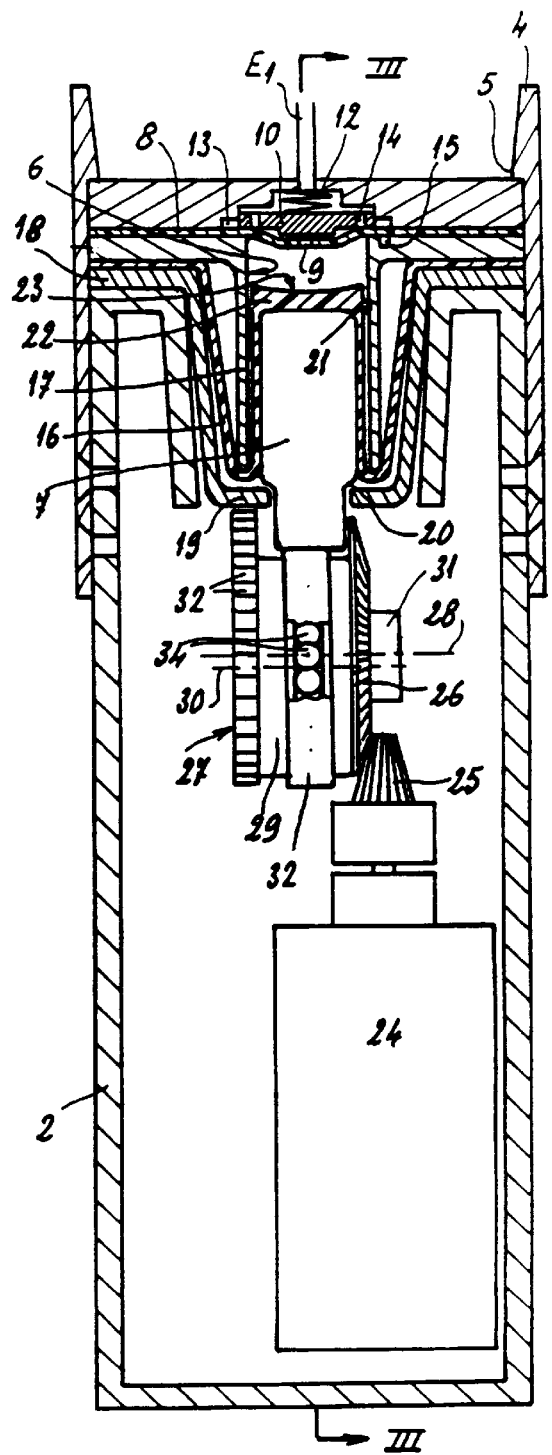
FIG. 2 is a section on an enlarged scale on the line II—II of FIG. 1.
Figure 3:
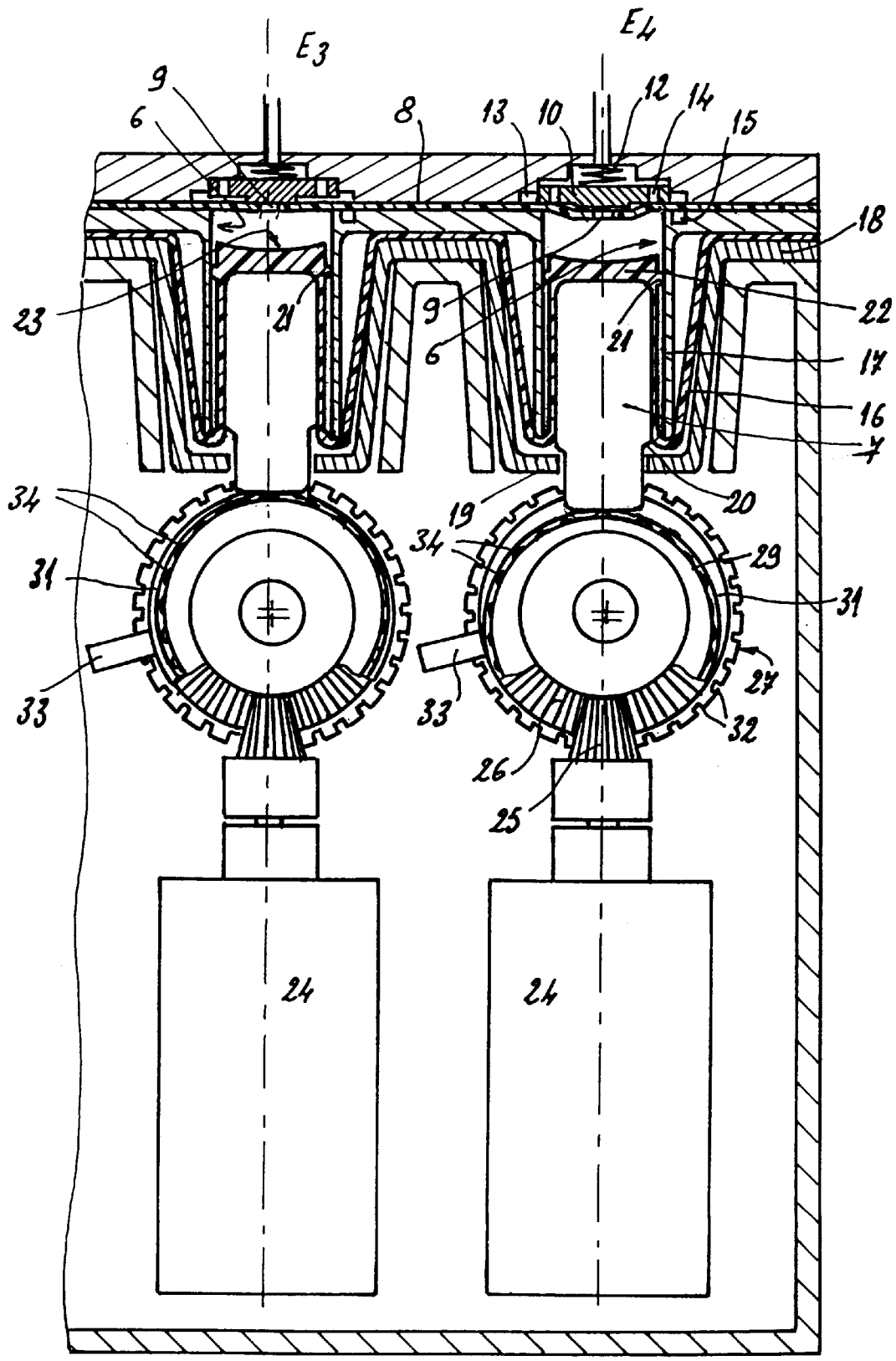
FIG. 3 is a part view, in longitudinal section, on the line III—III of FIG. 1, on an enlarged scale.

The infusion pump depicted in FIG. 1 is intended to convey four different liquids. It comprises a unit 2 containing means of programming the flow of each of the four liquids and for controlling the pistons of the metering devices. This unit also contains electric cells for powering the motors which move the pistons.

Mounted removably on this unit is a cassette 3 which corresponds to the part which draws up each liquid from inside a container which, for example, consists of a pouch made of synthetic material, a bottle comprising an air vent, or a syringe, and delivers this liquid into a tube connected by a catheter to the patient's body. The inlets of liquid to the inside of the cassette carry the references E1, E2, E3 and E4, while two outlets depicted carry the references S1 and S2. The cassette 3 is attached to the unit 2 by snap-fastening, using two elements 4 which extend the long faces of the unit 2, which have shoulders 5 intended to rest on the upper face of the cassette.

The structure of the cassette will not be described in detail because it is already known per se and corresponds to the arrangement described in document FR-A-2,689,014.

This cassette comprises four metering cylinders 6, in each of which there is a piston 7 capable of moving back and forth. The opposite end of the chamber 6 to the one via which the piston is operated is closed off by a membrane 8 comprising a central orifice 9 and against which there rests a disc 10 which is subject to the action of a spring 12 housed in a chamber 13 situated in the extension of the cylinder 6. The disc 10 has axial drillings 14 to allow the liquid to pass from the inlet orifice E1 towards the membrane 8. On the other side of the membrane 8 there is a port 15 for discharging the liquid, communicating with an outlet S1.

According to the essential feature of the invention, the piston is covered on its end face and on its lateral wall by an elastic membrane 16 mounted in tension over the piston and fixed by its peripheral edge to a stationary support independent of the piston.

In the embodiment depicted in the drawing, the membrane 16 extends over the interior face of the piece 17 delimiting the cylinder, runs up along the outside of this tubular piece 17, and is mechanically trapped between a horizontal return of the piece 17, and a horizontal return of a second piece 18 surrounding the piece 17. It should be noted that this second piece 18 at its lower end has a return 19 that forms a stop preventing the piston 7 from coming out, which piston for this purpose has a shoulder 20. The piston 7 is thereby associated with the cassette 3 and cannot be dissociated from the latter when a cassette is detached from a unit 2.

Close to its part that covers the front face of the piston, the membrane 16 has a peripheral ring 21 which seals it against the cylinder in which the piston is mounted.

It should be noted that the membrane 16, at the end face of the piston 7, has a thicker portion 22 in which there is formed a recess 23 of a concave shape that more or less complements the convex shape of the membrane 8 delimiting the metering cylinder. The elastic membrane 16 is made of elastomer or of latex.

Figure 4:
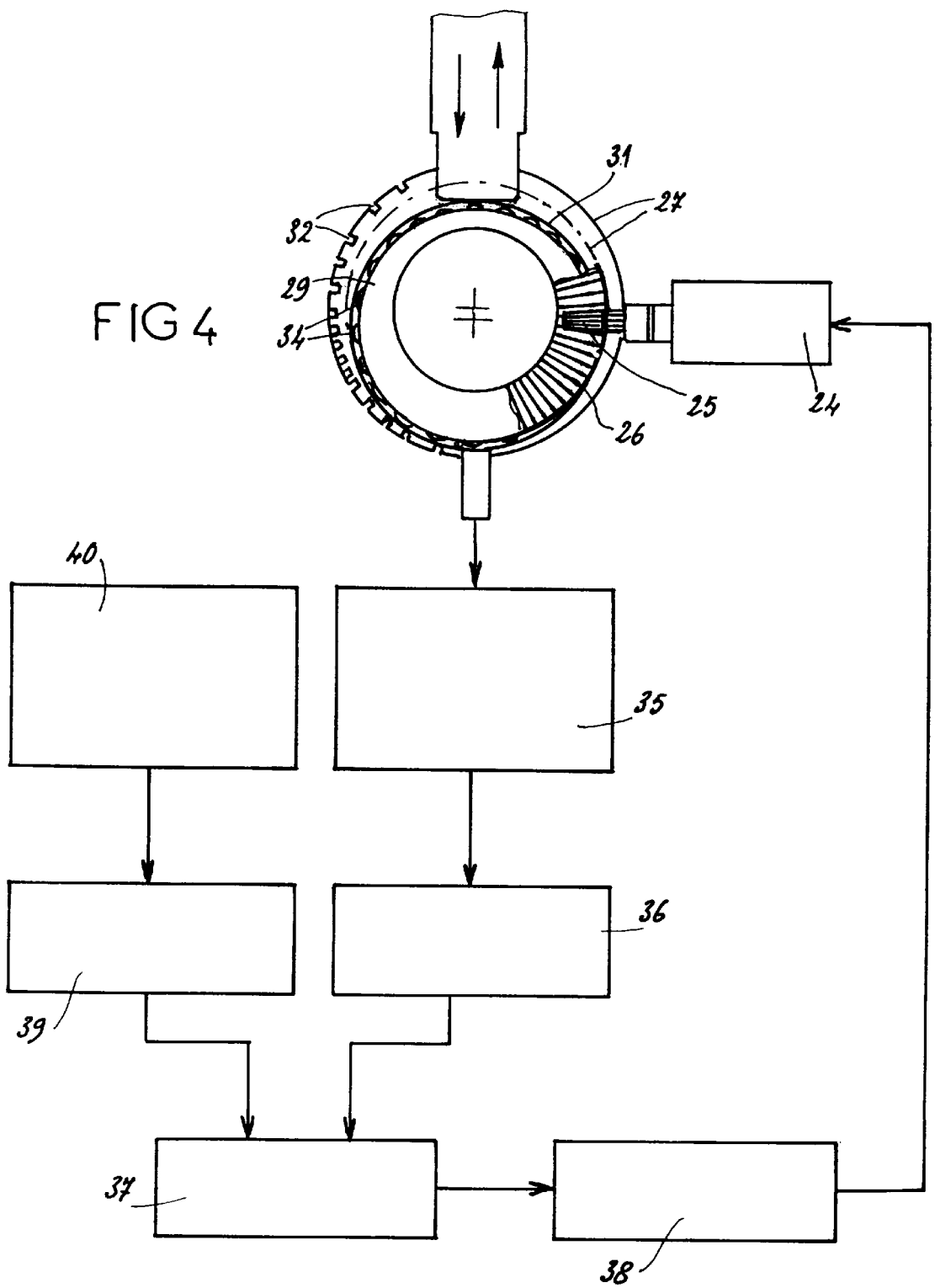
FIG. 4 is a detail of the device for controlling the movement.

The drive device for each piston comprises an electric motor 24, the output shaft of which is fitted with a bevel gear 25 meshing with the teeth 26 of a gear 27 the axis 28 of which is orthogonal to the axis of the piston. Fitted to this gear 27 is a eccentric disc 29, the offset axis 30 of which is parallel to the axis 28 of the gear 27 but offset with respect to this axis. On the axis of the motorized gear 27 is mounted a free-wheel mechanism 31 preventing any rotation of this disc in the opposite direction to that provided by the motor 24. The gear 27 also has peripheral slots 32 spread out on its periphery, which are identified as the gear 27 rotates by an encoder 33. The eccentric disc 29 is equipped on its periphery with a ball race 34, the cage 32 of which rests on the bottom end of the piston 7. As the disc 27 rotates, the eccentricity of the disc 29 results successively in a pushing force on the piston 7, then an elimination of this pushing force, in which situation the piston tends to increase the volume of the metering cylinder 6, bearing in mind the elastic return exerted by the membrane 16. The slots 32 are set out as a sinusoidal function so that the space between two slots always corresponds to the same volume despite the eccentricity of the disc 29 that controls the piston. FIG. 4 depicts the feedback-control of the motor 24 using the encoder 33. The encoder 33 is connected via a unit 35 to a pulse counter 36. This pulse counter provides information to a comparator 37, which also receives information from a clock 38 and from a theoretical pulse counter 39. This comparator acts on a power-supply unit 40 of the motor 24.

It is clear from the foregoing that a perfect seal between each liquid to be metered and the outside is provided by the membrane 16 arranged in each metering cylinder. Furthermore, the driving function of each membrane 16, which returns the piston when no action is exerted on it, allows the use of a simple drive device which consists simply in pushing the piston, without requiring a positive coupling between the drive means and the piston.

As goes without saying, the invention is not restricted simply to the one embodiment of this device which has been described hereinabove by way of example; on the contrary, it encompasses all the alternative forms thereof. Thus, in particular, the device for supplying liquid to each cylinder, and the elements associated with the membrane sealing this cylinder could differ, without in any way departing from the scope of the invention.

What is claimed is:

1. A pump for infusing medical liquids, comprising:
   at least one cylinder;
   at least one piston, a piston mounted in each cylinder of the at least one cylinder, for drawing up a liquid from a container and delivering the liquid into a tube connected to a patient; an opposite end of each cylinder to an end via which the piston is operated is closed by a leaktight and elastic membrane, the membrane comprising at least one opening for the passage of the liquid that allows the cylinder to be supplied with the liquid as the piston moves in a first direction that increases the volume of the cylinder;
   means for isolating the cylinder from the supply when the piston moves in a second, opposite direction that decreases the volume of the cylinder, the liquid then being discharged from the cylinder;
   each cylinder having at least one port for discharging the liquid close to the membrane,
   wherein the piston is covered on its end face and on its lateral wall by at least one elastic membrane mounted in tension over the piston, and the elastic membrane is fixed by its peripheral edge to a stationary support independent of the piston, the means of driving the piston comprises a device which exerts only a pushing force on the piston in the upward direction to make the piston decrease the volume of the cylinder, and the thickness of the membrane is greater at the end face of the piston than it is at the side wall thereof, the thicker region of the membrane has, on its outwardly-pointing face, a concave shaped recess that substantially complements the convex shape of the membrane delimiting the cylinder.

2. A pump according to claim 1, wherein the elastic membrane covering the piston is made of elastomer or of latex.

3. A pump according to claim 1, wherein the membrane has, close to the end face of the piston, a peripheral ring which seals it against the cylinder.

4. A pump according to claim 1, wherein the device for driving each piston comprises a disc with an axis orthogonal to the axis of the cylinder, the edge of which bears on the free end of the piston, and which is rotated about an axis parallel to and offset from its own axis.

5. A pump according to claim 4, wherein the disc, the edge of which bears against the free end of the piston, is fixed to a motorized disc one face of which has teeth interacting with a gear fixed to the output shaft of a gear motor unit, the motorized disc and the eccentric disc being fixed together with their respective axes offset.

6. A pump according to claim 5, wherein mounted on the axis of the motorized disc is a free-wheel mechanism that prevents the motorized disc from moving in the opposite direction to the direction in which it is driven by the motor under the effect of the pulling force of the membrane when the system is stopped or not powered.

7. A pump according to claim 5, wherein the motorized disc has peripheral slots intended to be detected by an optical encoder in order to determine the volume of liquid transferred, the optical encoder being connected to a pulse counter which is connected to a comparator that compares the measured pulses with a reference value in order to control the electrical supply to the motor.

8. A pump according to claim 7, wherein the peripheral slots in the motorized disc that are arranged as a sinusoidal function in order to take account of the offset between the axes of the motorized disc and the eccentric disc.

9. A pump according to claim 4, wherein the edge of the eccentric disc bearing against the piston is covered by a ball race.

10. A pump according to claim 1, further comprising a unit containing the programming means and the motor associated with each piston and a removable cassette allowing the various liquids to be drawn up and delivered, wherein each piston and the membrane covering each piston is mounted in the cassette.

* * * * *